United States Patent
Milenkova-Ilieva et al.

(10) Patent No.: US 11,970,530 B2
(45) Date of Patent: Apr. 30, 2024

(54) METHODS OF TREATING HOMOLOGOUS RECOMBINATION DEFICIENT CANCER

(71) Applicant: ASTRAZENECA AB, Sodertalje (SE)

(72) Inventors: Tsveta Petrova Milenkova-Ilieva, Cambridge (GB); Eric Pujade-Lauraine, Paris (FR); Isabelle Ray-Coquard, Lyons (FR)

(73) Assignee: ASTRAZENECA AB, Sodertalje (SE)

( * ) Notice: Subject to any disclaimer, the term of this patent is extended or adjusted under 35 U.S.C. 154(b) by 75 days.

(21) Appl. No.: 17/399,527

(22) Filed: Aug. 11, 2021

(65) Prior Publication Data

US 2022/0048983 A1    Feb. 17, 2022

Related U.S. Application Data

(60) Provisional application No. 63/065,132, filed on Aug. 13, 2020.

(51) Int. Cl.
| | |
|---|---|
| *C07K 16/22* | (2006.01) |
| *A61K 31/502* | (2006.01) |
| *A61K 45/06* | (2006.01) |
| *A61P 35/00* | (2006.01) |

(52) U.S. Cl.
CPC ............ *C07K 16/22* (2013.01); *A61K 31/502* (2013.01); *A61K 45/06* (2013.01); *A61P 35/00* (2018.01)

(58) Field of Classification Search
CPC ............ A61K 2039/505; A61K 31/502; A61K 45/06; A61P 35/00; C07K 16/22
See application file for complete search history.

(56) References Cited

PUBLICATIONS

Chen et al. ("Olaparib: a promising PARP inhibitor in ovarian cancer therapy."; Arch Gynecol Obstet 288, 367-374 (2013)) (Year: 2013).*
Madariaga et al. ("Wanna Get Away? Maintenance Treatments and Chemotherapy Holidays in Gynecologic Cancers." Am Soc Clin Oncol Educ Book. Jan. 2019;39:e152-e166) (Year: 2019).*
Randall ("A Retrospective Analysis of Real-World Tumor BRCA (tBRCA) TestingTrends in Ovarian Cancer (OC) Before and After PARP Inhibitor Approvals" Presented at the 17th Biennial Meeting of the International Gynecologic Cancer Society; Kyoto, Japan; Sep. 14-16, 2018) (Year: 2018).*
Burger et al. ("Incorporation of Bevacizumab in the Primary treatment of ovarian cancer"; N Engl J Med 2011;365:2473-83) (Year: 2011).*
Pujade-Lauraine et al. ("Olaparib tablets as maintenance therapy in patients with platinum-sensitive, relapsed ovarian cancer and a BRCA1/2 mutation (SOLO2/ENGOT-Ov21): a double-blind, randomised, placebo-controlled, phase 3 trial"; The Lancet Oncology, vol. 18, Issue 9,2017, pp. 1274-1284) (Year: 2017).*
Liu et al. (Combination cediranib and olaparib versus olaparib alone for women with recurrent platinum-sensitive ovarian cancer: a randomised phase 2 study, The Lancet Oncology, vol. 15, Issue 11, 2014, pp. 1207-1214 (Year: 2014).*
Trifanescu et al. ("Antiangiogenic Treatment in Ovarian Cancer in the Era of Evidenced-Based Medicine"; Maedica (Bucur). Sep. 2015;10(4):376-381) (Year: 2015).*
Ray-Coquard, et al, Olaparib plus Bevacizumab as First-Line Maintenance in Ovarian Cancer, NEJM, 2019.
PAOLA top line Aug. 14, 2019.

* cited by examiner

*Primary Examiner* — Ruixiang Li
(74) *Attorney, Agent, or Firm* — McDonnell Boehnen Hulbert & Berghoff LLP

(57) ABSTRACT

This disclosure relates to methods of treating homologous recombination (HR) deficient cancers, such as ovarian cancer, fallopian tube cancer, primary peritoneal cancer, breast cancer, and/or pancreatic cancer. This disclosure further relates to preventing, controlling or reducing hypertension and/or proteinuria in a subject receiving a therapeutically effective amount of bevacizumab therapy.

23 Claims, 4 Drawing Sheets

METHODS OF TREATING HOMOLOGOUS RECOMBINATION DEFICIENT CANCER

BACKGROUND OF THE DISCLOSURE

Field of the Disclosure

This disclosure relates to methods of treating homologous recombination (HR) deficient cancers, such as ovarian cancer, fallopian tube cancer, primary peritoneal cancer, breast cancer, and/or pancreatic cancer. This disclosure further relates to preventing, controlling or reducing hypertension and/or proteinuria in a subject receiving a therapeutically effective amount of bevacizumab therapy.

Description of Related Art

Homologous recombination has been shown to play an important role in repair of damage occurring at DNA replication forks in mammalian cells. Cells deficient in HR dependent DNA double-stranded break (DSB) repair pathway show retarded growth and exhibit higher level of genetic instability, which is believed to significantly contribute to the development of cancer in these cells. BRCA1 and BRCA 2 hereditary genes are just two out of many proteins in the HR dependent DNA DSB repair pathway. Other members of the HR dependent DNA DSB repair pathway include: ATM, BARD1, BRIP1, CHEK1, CHEK2, CDK12, FANCL, PALB2, PPP2R2A, RAD51B, RAD51C, RAD51D and RAD54L. Carriers of mutations in BRCA1 and/or BRCA2 are thus at elevated risk of breast and ovarian cancers, as well as pancreatic cancer and prostate cancer.

Today, ovarian cancer is the leading cause of death from gynecological cancers in the United States and Europe, ranking as the fifth most common cause of cancer death in women. The disease is predominantly diagnosed in postmenopausal women over 50 years (>80%) and the etiology is unknown although family history and a woman's reproductive history are important risk factors. Ovarian cancer remains one of the most difficult cancers to diagnose at an early curable stage; approximately 75% of patients present with advanced disease at initial diagnosis (Stage III or IV). Most patients die from their disease, with 5-year survival rates only 29% for advanced stages.

Cytoreductive surgery and platinum-based chemotherapy are considered the treatments of choice for patients with newly diagnosed advanced ovarian cancer. Even though most newly diagnosed advanced ovarian cancer patients achieve complete response (CR) at the end of first line treatment including surgery and platinum based chemotherapy, approximately 70% relapse within the first 3 years of diagnosis. Once ovarian cancer relapses, the disease becomes largely incurable.

Therefore, there remains a need for a first line maintenance treatment that provides a significant delay in progression and relapse, and potentially an improvement in cure rates, of ovarian and other HR deficient cancers.

SUMMARY OF THE DISCLOSURE

One aspect of the disclosure provides methods for treating ovarian cancer, fallopian tube cancer, primary peritoneal cancer, breast cancer, and/or pancreatic cancer in a subject. Such methods include:
administering to the subject a therapeutically effective amount of bevacizumab, and
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the therapeutically effective amount of olaparib is sufficient to prevent, control, or reduce hypertension in the subject as compared to hypertension in the subject when the subject receives bevacizumab alone.

Another aspect of the disclosure provides methods for preventing, controlling, or reducing hypertension in a subject receiving a therapeutically effective amount of bevacizumab. Such methods include:
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the therapeutically effective amount of olaparib is sufficient to prevent, control, or reduce hypertension in the subject as compared to hypertension in the subject when the subject receives bevacizumab alone.

Another aspect of the disclosure provides methods for treating ovarian cancer, fallopian tube cancer, primary peritoneal cancer, breast cancer, and/or pancreatic cancer in a subject. Such methods include:
administering to the subject a therapeutically effective amount of bevacizumab, and administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the therapeutically effective amount of olaparib is sufficient to prevent, control, or reduce proteinuria in the subject as compared to proteinuria in the subject when the subject receives bevacizumab alone.

Another aspect of the disclosure provides methods for preventing, controlling, or reducing proteinuria in a subject receiving a therapeutically effective amount of bevacizumab. Such methods include:
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the therapeutically effective amount of olaparib is sufficient to reduce proteinuria in the subject as compared to proteinuria in the subject when the subject receives bevacizumab alone.

Yet another aspect of the disclosure provides methods for treating ovarian cancer, fallopian tube cancer, primary peritoneal cancer, breast cancer, and/or pancreatic cancer in a subject. Such methods include:
administering to the subject a therapeutically effective amount of bevacizumab, and administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the progression free survival is at least about 4 months greater than for subjects receiving bevacizumab alone.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiment(s) of the disclosure and, together with the description, serve to explain the principles and operation of the disclosure.

DETAILED DESCRIPTION OF THE DISCLOSURE

Figure 1:
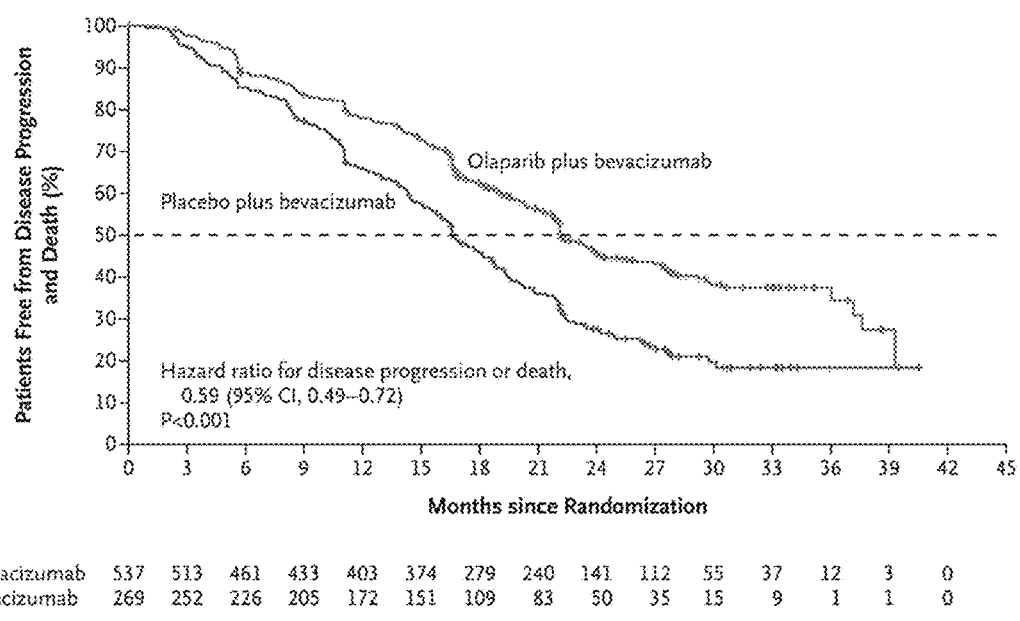
FIG. 1 shows progression-free survival (PFS) (Kaplan-Meier plot Full Analysis Set (FAS)) results of study provided in the example.

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. The present disclosure provides improvements in treating homologous recombination (HR) deficient cancers, such as ovarian cancer, fallopian tube cancer, primary peritoneal cancer, breast cancer, and/or pancreatic cancer. The present disclosure also provides improvements in preventing, controlling, or reducing hypertension and/or proteinuria in a subject receiving a therapeutically effective amount of bevacizumab therapy.

Thus, one aspect of the disclosure includes methods of treating ovarian cancer, fallopian tube cancer, primary peritoneal cancer, breast cancer, and/or pancreatic cancer in a subject. Such methods include:
administering to the subject a therapeutically effective amount of bevacizumab, and
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof.

In certain embodiments of the methods of the disclosure, the cancer is ovarian cancer or breast cancer. In certain embodiments of the methods of the disclosure, the cancer is ovarian cancer. In certain embodiments, the cancer is advanced epithelial ovarian cancer. In certain embodiments, the cancer is high-grade serous ovarian cancer. In certain embodiments, the cancer is high-grade endometrioid ovarian cancer. In certain embodiments, the cancer is epithelial ovarian cancer comprising a gBRCA1 or a gBRCA2 mutation. In certain embodiments of the methods of the disclosure, the cancer is fallopian tube cancer. In certain embodiments of the methods of the disclosure, the cancer is primary peritoneal cancer.

In certain embodiments of the methods of the disclosure, the cancer is ovarian (such as advanced epithelial ovarian), fallopian tube, or primary peritoneal cancer.

Another embodiment of the disclosure provides methods where the cancer is homologous recombination deficient (HRD) cancer. For example, whether the cancer is HRD positive can be determined by Myriad Genetics myChoice® HRD or myChoice® HRD Plus assay.

In certain embodiments, the cancer cells comprise HRD gene mutation selected from BRCA1, BRCA2, ATM, BRIP1, BARD1, CDK12, CHEK1, CHEK2, FANCL, PALB2, PPP2R2A, RAD51B, RAD51C, RAD51D, and RAD54L gene mutation. In certain embodiments, the cancer cells comprise a BRCA1, a BRCA2, and/or an ATM gene mutation. In certain embodiments, the cancer cells comprise a BRCA1 and/or a BRCA2 gene mutation. For example, in certain embodiments, the cancer cells comprise a tBRCA gene mutation.

In certain embodiments of the methods of the disclosure, the cancer comprises homologous recombination deficiency (HRD)-positive status defined by a deleterious or suspected deleterious BRCA mutation and/or genomic instability.

In certain embodiments of the methods of the disclosure, the cancer is ovarian (such as advanced epithelial ovarian), fallopian tube, or primary peritoneal cancer, the cancer comprising homologous recombination deficiency (HRD)-positive status defined by a deleterious or suspected deleterious BRCA mutation and/or genomic instability.

As used herein, the terms "individual," "patient," or "subject" are used interchangeably, refers to any animal, including mammals, and most preferably humans.

The methods of disclosure are useful as a first line maintenance treatment. Thus, in certain embodiments of the methods of the disclosure, the subject has previously completed a first line of therapy. The methods of the disclosure, in certain embodiments, may provide a delay in progression and relapse of cancer of subjects that have previously completed a first line of chemotherapy. Such subject may be in complete or partial response to the first line of chemotherapy. For example, in certain embodiments, the subject has previously completed a first line platinum- and/or taxane-based chemotherapy. Examples of platinum-based chemotherapy include, but are not limited to, carboplatin, cisplatin, oxaliplatin, and the like. Examples of taxane-based chemotherapy include, but are not limited to, paclitaxel and docetaxel. In certain embodiments, the subject has previously completed a first line platinum- and taxane-based chemotherapy. In certain embodiments, the subject previously received between 6 and 9 cycles of first line platinum- and/or taxane-based chemotherapy. In certain embodiments, the subject received a last cycle of first line platinum- and/or taxane-based chemotherapy between 3 weeks and 9 weeks prior to administering olaparib. In certain embodiments, the subject previously received at least 3 cycles of bevacizumab in combination with first line platinum- and/or taxane-based chemotherapy.

In certain embodiments of the methods of the disclosure, the subject has previously completed a first line platinum-based chemotherapy and is in complete or partial response to the first line of chemotherapy.

In certain embodiments of the methods of the disclosure, the subject has ovarian (such as advanced epithelial ovarian), fallopian tube, or primary peritoneal cancer, the cancer comprising homologous recombination deficiency (HRD)-positive status defined by a deleterious or suspected deleterious BRCA mutation and/or genomic instability, and the subject previously completed a first line platinum-based chemotherapy and is in complete or partial response to the first line of chemotherapy.

As will be discussed in more detail below, the methods of the disclosure may be particularly useful in subject having high blood pressure (hypertension) or being predisposed to hypertension. Thus, in certain embodiments, the subject has hypertension or is predisposed to hypertension (e.g., by having one or more risk factors in developing hypertension, such as age, weight, family history, etc.). As used herein, "hypertension" is higher than normal blood pressure with readings of systolic blood pressure ≤120 mmHg and/or diastolic blood pressure ≤80 mmHg. In certain embodiments, the subject has hypertension. In certain other embodiments, the methods of the disclosure further comprise identifying the subject having hypertension. In certain embodiments, the subject is identified as having hypertension is at least Grade 3 as determined by Common Terminology Criteria for Adverse Events (CTCAE) (version 4.03) (e.g., the subject having at least systolic blood pressure ≥160 mmHg or diastolic blood pressure ≥100 mmHg).

As provided above, bevacizumab is administered in the methods of the disclosure. Bevacizumab, also sold as AVASTIN®, is a vascular endothelial growth factor inhibitor. Bevacizumab is a recombinant humanized monoclonal IgG1 antibody that contains human framework regions and murine complementarity-determining regions. Approximately 93% of the amino acid sequence of bevacizumab, including most of the framework regions, is derived from human IgG1, and about 7% of the sequence is derived from the murine antibody. Bevacizumab has an approximate molecular weight of 149 kDa and is glycosylated. Bevacizumab is produced in a mammalian cell (Chinese Hamster Ovary) expression system. AVASTIN® can be obtained from Genentech Corp. or Roche Corp. or as described elsewhere (U.S. Pat. No. 6,054,297 and Presta et al. (1997) Cancer Res. 57:4593-4599).

Therapeutically effective amount of bevacizumab has been previously established. For example, in certain embodiments, bevacizumab may be administered in in the range of about 10 to 20 mg/kg of body weight every 3 weeks. In certain embodiments, the therapeutically effective amount of bevacizumab is about 15 mg/kg of body weight every 3 weeks. Likewise, the duration of bevacizumab administration has been previously established. For example, in certain embodiments, bevacizumab is administered at no more than 22 cycles in total.

The methods of the disclosure also require administration of olaparib. As used herein, "olaparib" refers to 4-[(3-{[4-(cyclopropane-carbonyl)piperazine-1-yl]carbonyl}-4-fluorophenyl)methyl]-2H-phthalazin-1-one, or a hydrate, solvate, or prodrug thereof. 4-[(3-{[4-(cyclopropane-carbonyl)piperazine-1-yl]carbonyl}-4-fluorophenyl)methyl]-2H-phthalazin-1-one, having the following structure, is disclosed in International Publication No. WO 2004/080976 A1, incorporated by reference herein.

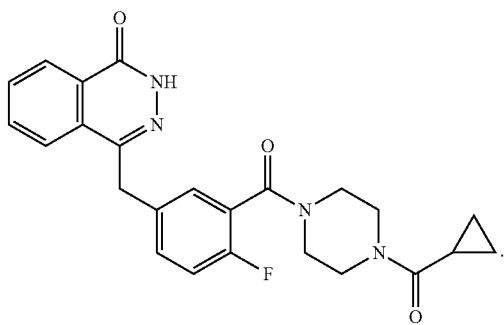 [SMILES: O=C(c1cc(Cc2n[nH]c(=O)c3ccccc23)ccc1F)N1CCN(C(=O)C2CC2)CC1]

Olaparib is administered preferably in the form of a pharmaceutical composition. As with bevacizumab, therapeutically effective amount of olaparib has been previously established. In certain embodiments, the therapeutically effective amount of olaparib is in the range of about 400 to 800 mg per day. For example, in certain embodiments, olaparib is administered in an amount of about 600 mg daily (e.g., about 300 mg taken twice daily).

It is worth noting that hypertension is a known adverse drug reaction for subjects receiving bevacizumab (e.g., as compared to the subjects receiving chemotherapy alone). Across various clinical studies, the incidence of severe hypertension ranged from 5% to 18% for subjects receiving bevacizumab. In the present study, incidence of CTCAE Grade ≥3 hypertension was about 30% for subjects receiving bevacizumab alone (i.e., receiving bevacizumab without also receiving olaparib).

The inventors unexpectedly found that administering olaparib, in addition to bevacizumab, is sufficient to prevent, control or reduce hypertension in the subject as compared to the subject receiving bevacizumab alone (i.e., receiving bevacizumab without also receiving olaparib). Therefore, in the methods of the disclosure the therapeutically effective amount of olaparib is sufficient to prevent, control, or reduce hypertension in the subject as compared to hypertension in the subject when the subject receives bevacizumab alone (i.e., receiving bevacizumab without also receiving olaparib).

In certain embodiments, the therapeutically effective amount of olaparib prevents developing CTCAE Grade 2, Grade 3, or Grade 4 hypertension. In certain embodiments, the therapeutically effective amount of olaparib prevents developing CTCAE Grade 3 or Grade 4 hypertension.

In certain embodiments, the therapeutically effective amount of olaparib reduces CTCAE Grade 2, Grade 3, or Grade 4 hypertension (e.g., reduces by one or more Grades). In certain embodiments, the therapeutically effective amount of olaparib reduces CTCAE Grade 3 or Grade 4 hypertension (e.g., reduces to Grade 2 and lower).

In certain embodiments, the therapeutically effective amount of olaparib controls systolic blood pressure in the subject. For example, the systolic blood pressure may be maintained at ≤140 mmHg. In another example, the systolic blood pressure may be maintained at ≤130 mmHg. In another example, the systolic blood pressure may be maintained at ≤120 mmHg.

In certain embodiments, the therapeutically effective amount of olaparib reduces systolic blood pressure in the subject. For example, the systolic blood pressure may be reduced to ≤140 mmHg. In another example, the systolic blood pressure may be reduced to ≤130 mmHg. In another example, the systolic blood pressure may be reduced to ≤120 mmHg.

In certain embodiments, the therapeutically effective amount of olaparib controls diastolic blood pressure in the subject. For example, the diastolic blood pressure may be maintained at ≤90 mmHg. In another example, the diastolic blood pressure may be maintained at in a range of 80 to 90 mmHg. In another example, the diastolic blood pressure may be maintained at ≤80 mmHg.

In certain embodiments, the therapeutically effective amount of olaparib reduces diastolic blood pressure in the subject. For example, the diastolic blood pressure may be reduced to ≤90 mmHg. In another example, the diastolic blood pressure may be reduced to a range of 80 to 90 mmHg. In another example, the diastolic blood pressure may be reduced to ≤80 mmHg.

The subject may be predisposed to hypertension or the subject may develop hypertension with bevacizumab treatment. In certain embodiments, the methods of the disclosure further comprise identifying a subject that may be predisposed or may develop hypertension. For example, the subject may be identified by measuring blood pressure in the subject (e.g., prior and/or during the treatment). In another example, the subject may be identified by evaluating the subject's medical history and/or hereditary factors.

In certain embodiments, the methods of the disclosure further comprise monitoring hypertension (e.g., by measuring blood pressure in the subject).

Generally, to control hypertension, one of more antihypertensive drugs are administered (e.g., concomitantly) in the methods of the disclosure. Antihypertensive drugs are generally known in the art. Classes of antihypertensive drugs used to manage hypertension, including hypertension arising as a side effect of bevacizumab treatment, comprise diuretics, beta-blockers, ACE inhibitors, Angiotension II receptor blockers, calcium channel blockers, alpha blockers, alpha-2 receptor agonists, combined alpha and beta-blockers, central agonists, peripheral adrenergic inhibitors, vasodilators. Calcium channel blockers such as amlodipine frequently prescribed. Anti-hypertensive naïve patients who develop hypertension during bevacizumab treatment are frequently treated with 5 mg amlodipine daily. Patients with pre-existing hypertension who develop more serious hypertension on treatment with bevacizumab may be treated with a more intensive anti-hypertensive regime, for example by stepping up their existing treatment or by moving onto an alternative drug. Thus, in certain embodiments, the therapeutically effective amount of olaparib is sufficient to reduce or eliminate administration of one of more antihypertensive drugs. For example, in certain embodiments, the methods of the disclosure have no concomitant administration of one of more antihypertensive drugs. In certain other embodiments in the methods of the disclosure, one or more antihypertensive drugs are administered at a level that is at least 20% less (e.g., at least 30% less, or at least 40% less, or at least 50% less, or at least 75% less) than their established therapeutic amount. In certain embodiments, the methods of the disclosure further comprise monitoring hypertension (e.g., by measuring blood pressure in the subject) and administering one of more antihypertensive drugs at a level that is at least 20% less (e.g., at least 30% less, or at least 40% less, or at least 50% less, or at least 75% less) than their established therapeutic amount. In embodiments, the disclosure makes available a method of reducing the probability of bevacizumab-induced hypertension in a population of patients (or in an individual patient) treated for cancer using bevacizumab, comprising administering an effective amount of olaparib and bevacizumab Another known adverse drug reaction for subjects receiving bevacizumab (e.g., as compared to the subjects receiving chemotherapy alone) is proteinuria. For example, Grade 3 (defined as urine dipstick 4+ or ≥3.5 grams of protein per 24 hours) proteinuria to nephrotic syndrome ranged from 0.7% to 7% in clinical studies. The overall incidence of proteinuria (all grades) was 20% as assessed in Study BO17705. Median onset of proteinuria was 5.6 months after initiating bevacizumab. Proteinuria did not resolve in 40% of patients after median follow-up of 11.2 months and required discontinuation of bevacizumab in 30% of the patients who developed proteinuria.

The inventors also unexpectedly found that administering olaparib, in addition to bevacizumab, is sufficient to prevent, control, or reduce proteinuria in the subject as compared to the subject receiving bevacizumab alone (i.e., receiving bevacizumab without also receiving olaparib). Therefore, in the methods of the disclosure the therapeutically effective amount of olaparib is sufficient to prevent, control, or reduce proteinuria in the subject as compared to proteinuria in the subject when the subject receives bevacizumab alone (i.e., receiving bevacizumab without also receiving olaparib). In certain embodiments, the subject develops proteinuria with bevacizumab treatment.

In certain embodiments, the therapeutically effective amount of olaparib prevents developing CTCAE Grade 2 or Grade 3 proteinuria. In certain embodiments, the therapeutically effective amount of olaparib prevents developing CTCAE Grade 3 or Grade 4 proteinuria. In certain embodiments, the therapeutically effective amount of olaparib reduces CTCAE Grade 2 or Grade 3 proteinuria (e.g., reduces by one or more Grades). In certain embodiments, the therapeutically effective amount of olaparib reduces CTCAE Grade 3 proteinuria (e.g., reduces to Grade 2 and lower).

The inventors also unexpectedly found that administering olaparib is sufficient to improve progression free survival (or other key therapeutic metric such as overall survival, time to earliest progression according to modified Response Evaluation Criteria in Solid Tumours (RECIST version 1.1), or cancer antigen-125, or death; time from randomisation to first subsequent therapy or death; time from randomisation to second progression; time from randomisation to second subsequent therapy or death; etc.) in the subject as compared to the subject receiving bevacizumab alone (i.e., receiving bevacizumab without also receiving olaparib). For example, in the overall subject population, the inventors found that the progression free survival is at least about 4 months greater than for subjects receiving bevacizumab alone. In certain embodiments, the progression free survival is about 4 to 6 months greater, or about 4 to 8 months greater, or about 4 to 12 months greater. In certain embodiments, wherein the subject has BRCA mutation cancer, the progression free survival is about 10 to 20 months greater (e.g., about 10 to 15 months greater, or about 12 to 15 months greater, or at least about 12 months greater, or at least about 15 months greater). In certain embodiments, wherein the subject has HRD+ cancer, the progression free survival is about 10 to 25 months greater (e.g., about 15 to 25 months greater, or about 18 to 22 months greater, or at least about 10 months greater, or at least about 20 months greater). In certain embodiments, wherein the subject has HRD+ BRCA mutation cancer, the progression free survival is about 15 to 25 months greater (e.g., about 18 to 22 months greater, or about 18 months greater, or about 20 months greater).

In certain embodiments, in the overall subject population, the progression free survival is at least about 20 months. In certain embodiments, the progression free survival is about 18 to 24 months, or about 20 to 24 months, or about 20 to 22 months. In certain embodiments, wherein the subject has BRCA mutation cancer, the progression free survival is at least about 35 months (e.g., about 35 to 40 months, or about 36 to about 38 months, or at about 37 months). In certain embodiments, wherein the subject has HRD+ BRCA mutation cancer, the progression free survival is at least about 35 months (e.g., about 35 to 40 months, or about 36 to about 38 months, or at about 37 months). In certain embodiments, wherein the subject has HRD+ cancer without BRCA mutation, the progression free survival is at least about 26 months (e.g., about 26 to 30 months, or about 27 to about 30 months, or at about 28 months).

As used herein, the phrase "therapeutically effective amount" or "effective amount" refers to the amount of active compound or pharmaceutical agent that elicits the biological or medicinal response that is being sought in a tissue, system, individual or human by a researcher, medical doctor or other clinician.

In certain embodiments, an effective amount can be an amount suitable for
(i) inhibiting the progression the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder; or
(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease.

EXAMPLE

The methods of the disclosure are illustrated further by the following example, which is not to be construed as limiting the disclosure in scope or spirit to the specific procedures and compounds described in them.

Study Design

Over the past decade, the most important improvement of the established systemic first line treatment with platinum-taxane chemotherapy has been the introduction of novel targeted therapies in the front-line setting. Ovarian cancer is a highly vascular tumor, and markedly elevated serum VEGF levels have been associated with advanced stage ovarian cancer, high-grade histology, increased incidence of metastases, occurrence of large volume ascites and decreased survival. The VEGF inhibitor, bevacizumab (Avastin®), in combination with carboplatin and paclitaxel followed by bevacizumab maintenance, is the first targeted non-chemotherapy treatment approved in the first line ovarian cancer setting and has become an established standard of care, regardless of their BRCA mutation status.

In addition to being a VEGF responsive tumor, the high prevalence of homologous recombination repair- (HRR-) deficiency in high-grade epithelial ovarian cancer, provides a strong rationale for targeted treatment with polyadenosine 5'diphosphoribose polymerase (PARP) inhibitors in this patient population. Olaparib, a potent PARP inhibitor, exploits deficiencies in deoxyribonucleic acid (DNA) repair pathways to preferentially kill cancer cells with these deficits compared to normal cells. Olaparib was first approved in 2014 as a maintenance treatment in patients with BRCAm platinum-sensitive relapsed ovarian cancer who were in response to platinum-based chemotherapy.

The rationale for the study design was based on available non-clinical and clinical data to combine 2 effective targeted treatments in ovarian cancer after completion of platinum-based chemotherapy, in the first line maintenance treatment setting where improvement in clinical outcomes can be most impactful to patients, providing a significant delay in progression and relapse, and potentially an improvement in cure rates.

The study design was put into practice as the PAOLA-1/ENGOT-ov25 trial (NCT02477644), which was a randomised, double-blind, international phase III trial that enrolled patients with newly diagnosed, FIGO stage III-IV, high-grade serous or endometrioid ovarian cancer, fallopian tube or primary peritoneal cancer. The claimed embodiments are based on data and observations arising during the PAOLA-1/ENGOT-ov25 trial, and also described by Ray-Coquard I et al. ("Olaparib plus Bevacizumab as First-Line Maintenance in Ovarian Cancer." *N Engl J Med.* 2019; 381(25): 2416-2428; incorporated by reference herein in its entirety), which data and observations are described below.

Study Treatment Dose and Formulation

Patients were randomized in a 2:1 ratio to the treatments as specified below:
1. Olaparib tablets orally 300 mg twice daily (bd)
2. Placebo tablets orally 300 mg bd Bevacizumab, as standard of care therapy, was administered in both arms as follows: 15 mg/kg of body weight every 3 weeks (Q3W), for a total duration of up to 15 months/22 cycles (including combination with platinum-based chemotherapy).

The "overall study duration" phase was defined as from the first dose of olaparib or placebo until the last dose of olaparib or placebo+30 days (to account for the 30 day follow-up period). The "combination phase only" was defined as from the first dose of combination treatment (bevacizumab and olaparib or bevacizumab and placebo) until the last dose of bevacizumab+21 days whilst on combination treatment (to account for 3 weekly interval of bevacizumab).

Overall, the median total duration of exposure to olaparib in the olaparib/bevacizumab arm was longer than exposure to placebo in the placebo/bevacizumab arm (17.3 vs 15.6 months, respectively) and consistent with the 2 year olaparib/placebo treatment cap and time to first progression. In the Combination Phase only, the median total duration of treatment in the olaparib/bevacizumab arm was the same as the placebo/bevacizumab arm (10.6 months each). The median total duration of exposure to bevacizumab was similar between the arms (11.0 months in the olaparib/bevacizumab arm and 10.4 months in the placebo/bevacizumab arm). The majority of patients remained on the full dose of olaparib for the duration of treatment.

Patient Population

Patients included in the study were female patients with newly diagnosed advanced (FIGO (International Federation of Gynaecology and Obstetrics) Stage IIIB, IIIC or IV) ovarian cancer, primary peritoneal cancer and/or fallopian tube cancer that was histologically confirmed as: (a) high-grade serous, or (b) high-grade endometrioid, or (c) other epithelial non mucinous ovarian cancer in a patient with gBRCA1 or 2 deleterious mutation.

Additionally, patents had completed first line platinum-taxane chemotherapy prior to randomization. Specifically, the platinum-taxane based regimen consisted of a minimum of 6 and a maximum of 9 treatment cycles; however, if platinum-based therapy was discontinued early as a result of non-haematological toxicity specifically related to the platinum regimen, (i.e., neurotoxicity, hypersensitivity, etc.), patients must have received a minimum of 4 cycles of the platinum regimen. Intravenous, intraperitoneal, or neoadjuvant platinum based chemotherapy was also allowed; for weekly therapy, 3 weeks was considered to be 1 cycle.

Prior to randomization, patients received a minimum of 3 cycles of bevacizumab in combination with the last 3 cycles of platinum-based chemotherapy. In patients who had undergone interval debulking surgery (IDS), a minimum of 2 cycles of bevacizumab in combination with the last 3 cycles of platinum-based chemotherapy must have been received. Bevacizumab treatment was to be administered at a dose of 15 mg/kg every 3 weeks (Q3W) for up to a total of 15 months.

Prior to randomization, patients had no evidence of disease (NED) or had been in clinical complete response (CR) or in partial response (PR) following first line treatment. There should have been no clinical evidence of disease progression (physical exam, imaging, or cancer antigen-125 (CA-125)) throughout the first line treatment and prior to study randomization.

Finally, patients were randomized at least 3 weeks and no more than 9 weeks after their last dose of chemotherapy (last dose is the day of the last infusion) and all major toxicities from the previous chemotherapy were resolved.

Post-Randomization Tumor Biomarker Testing at Myriad

Tumor samples from the patients were tested post-randomization (but prior to database lock) using the Myriad myChoice® HRD Plus test in order to investigate efficacy in pre-defined biomarker subgroups. The Myriad myChoice® HRD Plus test is delivered from a single central laboratory in Salt Lake City, Utah; it detects and classifies the following biomarkers simultaneously in tumor tissue:

Sequence variants and large rearrangements in BRCA1 and BRCA2, as well as an additional 13 HRR genes: ATM, BARD1, BRIP1, CHEK1, CHEK2, CDK12, FANCL, PALB2, PPP2R2A, RAD51B, RAD51C, RAD51D and RAD54L.

Myriad HRD score was designed to identify a comprehensive signature/genomic scar indicating homologous recombination deficiency by testing genome-wide single nucleotide variants. The Myriad HRD score is determined by measuring 3 elements: loss of heterozygosity, telomeric allelic imbalance and large-scale state transitions.

Myriad HRD status is based on the Myriad HRD score and tBRCAm status. A positive Myriad HRD status is determined either by presence of a tBRCA1/2 mutation or by an HRD score at or above a pre-specified cut-off in the absence of a BRCA1/2 mutation. The Myriad HRD cut-off of 42 detects 95% of BRCAm tumors and has been extensively investigated as a biomarker of PARP inhibitor benefit in ovarian cancer. The cut-off of 42 has now been FDA-approved for another PARP inhibitor for the treatment of relapsed ovarian cancer (Myriad myChoice® HRD test offered under the name myChoice® CDx). Reducing the cut-off to 33, enables detection of 99% of BRCAm tumors and retrospective analyses from 2 clinical studies raised the possibility that a 33 cut-off may provide greater precision in determining patients who may benefit from PARP inhibitor treatment.

Statistical and Analytical Methods

Statistical analyses were performed by the Biostatistics Group, AstraZeneca. All calculations were performed with SAS® software Version 9.4 (SAS Institute, Inc., Cary, North Carolina).

The data cut-off (DCO) for the analysis of progression-free survival (PFS) PFS is time from randomization to first progression or death according to modified Response Evaluation Criteria in Solid Tumours (RECIST version 1.1). PFS took place when 474 progression events had occurred (58.8% maturity), approximately 45 months after the first patient was randomized. At this DCO, all efficacy, QoL and safety variables were analyzed, as appropriate, based on the amount of data available at that time.

Overall Survival (OS) and Vital Signs Measurements

OS was defined as the time from the date of randomization until death due to any cause. Any patient not known to have died at the time of analysis was censored based on the last recorded date on which the patient was known to be alive.

Results

PFS (based on investigator assessment) was the primary variable for the study and was analyzed based on the primary data cut-off using the investigator assessment population.

At the time of data cut-off, taking into account the pre-specified rules for declaring PFS events, there were 474 PFS events (58.8% maturity) with a higher proportion on the placebo/bevacizumab arm than the olaparib/bevacizumab arm (72.1% placebo/bevacizumab vs 52.1% olaparib/bevacizumab, respectively). Twelve of the PFS events were deaths in the absence of Response Evaluation Criteria in Solid Tumors (RECIST) progression (excluding censoring due to 2 or more missed RECIST visits). The majority of patients in both arms progressed due to developing new lesions.

Overall, 47.9% of patients in the olaparib/bevacizumab arm vs 27.9% of patients in the placebo/bevacizumab arm were not classified as having progressed at the time of analysis.

As shown in Table 1, the analysis of PFS showed a statistically significant and clinically meaningful improvement for patients treated with olaparib compared with placebo, when added to bevacizumab, as evidenced by the magnitude of effect: a 41% reduction in the risk of disease progression or death. The median was 22.1 months for olaparib/bevacizumab-treated patients vs. 16.6 months for placebo/bevacizumab-treated patients. Based on the KM estimates, the percentage of patients who remained progression free in the olaparib/bevacizumab arm was 78.0% at 12 months and 46.0% at 24 months compared with 65.6% and 27.7% of patients in the placebo/bevacizumab arm, respectively. Median follow-up for PFS defined as time from randomization to date of censoring was 22.7 and 24.0 months in the olaparib/bevacizumab and placebo/bevacizumab arms, respectively. Progression occurred on treatment for 56.8% of patients on olaparib/bevacizumab compared with 71.6% of patients on placebo/bevacizumab.

TABLE 1

Summary of analysis of PFS

|  | Olaparib/bevacizumab (N = 537) | Placebo/bevacizumab (N = 269) |
|---|---|---|
| n (%) of events[a] | 280 (52.1) | 194 (72.1) |
| Treatment effect |  |  |
| Median PFS (95% CI), months[b] | 22.1 (21.8, 24.1) | 16.6 (15.4, 18.6) |
| HR[c] | 0.59 | |
| 95% CI[c] | 0.49, 0.72 | |
| 2-sided p-value[d] | <0.0001 | |
| Progression free at 6 months (%)[b] | 88.8 | 85.3 |
| Progression free at 12 months (%)[b] | 78.0 | 65.6 |
| Progression free at 18 months (%)[b] | 62.3 | 45.8 |
| Progression free at 24 months (%)[b] | 46.0 | 27.7 |
| Median (IQR) follow-up for PFS, months[e] | 22.7 (18.0, 27.7) | 24.0 (18.7, 27.7) |

[a]PFS was defined as time from randomization until the date of objective radiological disease progression according to modified RECIST 1.1 or death;
[b]Calculated using KM techniques;
[c]Estimated from a stratified Cox proportional hazards model stratified by first line treatment outcome and tBRCA status;
[d]Determined using log-rank test stratified by first line treatment outcome and tBRCA status;
[e]Time from randomization to date of censoring.

Figure 2:
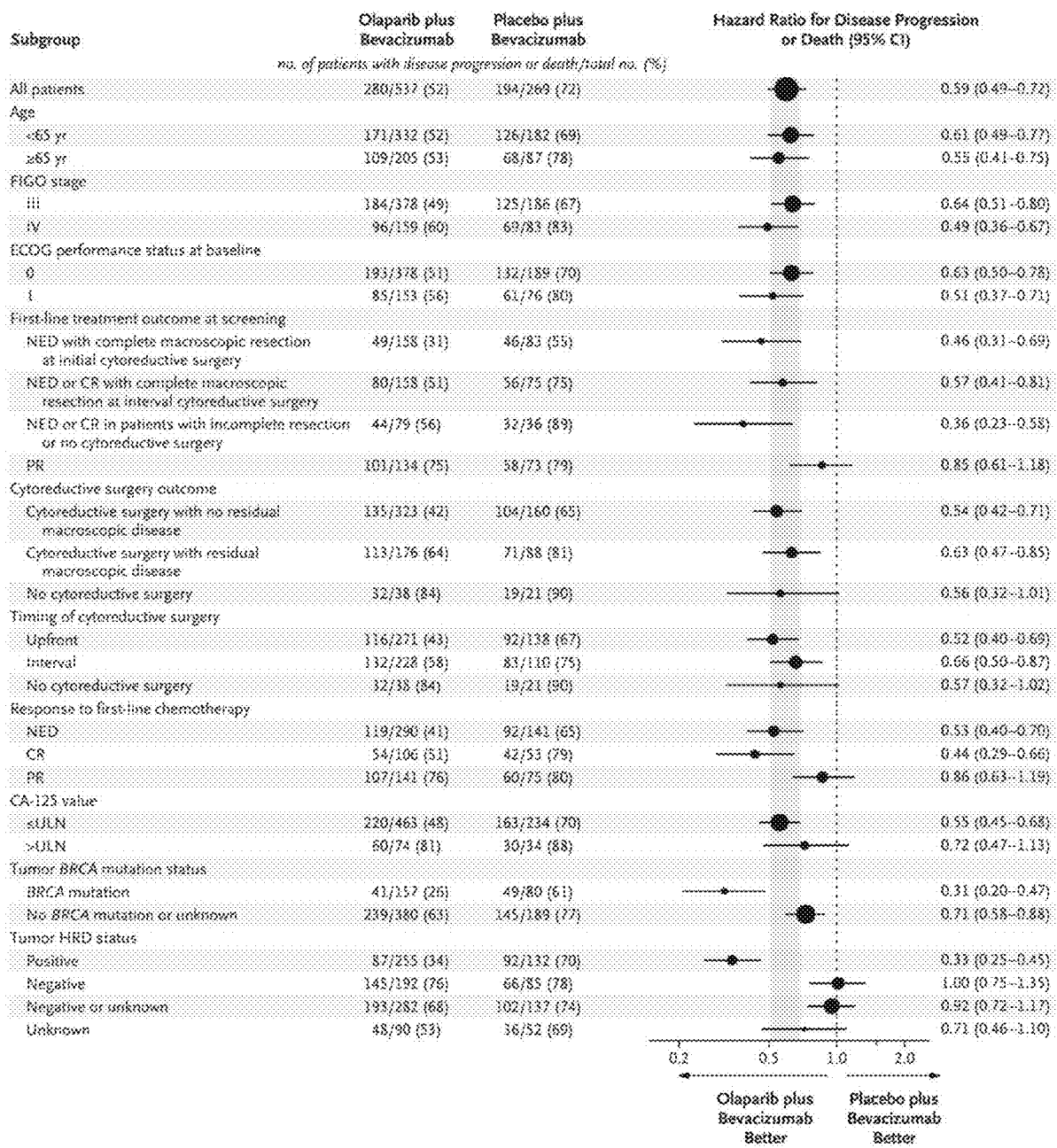
FIG. 2 shows subgroup analysis of PFS results of study provided in the example.

The Kaplan-Meier plot for the investigator-assessed PFS by RECIST is presented in FIG. 1. The 2 curves start to separate at approximately 3 months from randomization and maintain the separation in favor of the olaparib/bevacizumab-treated patients up to 36 months. At the time of the data cut-off, few patients were at risk beyond this time point. According to Kaplan-Meier estimates, the percentage of patients in the olaparib-plus-bevacizumab group and the placebo-plus-bevacizumab group who were free from disease progression and death was 78% and 66%, respectively, at 12 months; 62% and 46%, respectively, at 18 months; and 46% and 28%, respectively, at 24 months. The dashed horizontal line indicates the median value. Results of subgroup analyses of progression-free survival showed a benefit in the majority of predefined subgroups (FIG. 2).

Second progression or death (PFS2) events were based on radiological, CA-125 or symptomatic progression (as assessed by the investigator) or death. In both treatment arms, of the patients who had a second progression, the majority were based on radiological assessment. At the time of the PFS analysis, the PFS2 data were 39.1% mature (315 events/806 patients). Overall, 63.5% of patients in the olaparib/bevacizumab arm vs 55.8% of patients in the placebo/bevacizumab arm were not classified as having had a second progression at the time of analysis.

Figure 3A:
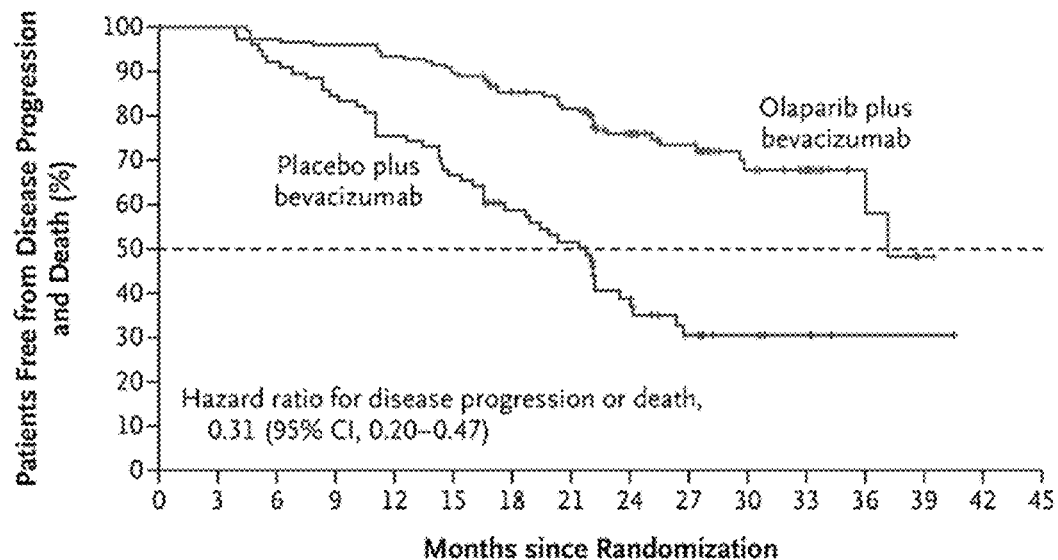
FIGS. 3A-3D show Kaplan-Meier estimates of PFS according to tumor BRCA mutation status and Homologous-Recombination Deficiency (HRD) Status.
Figure 3B:
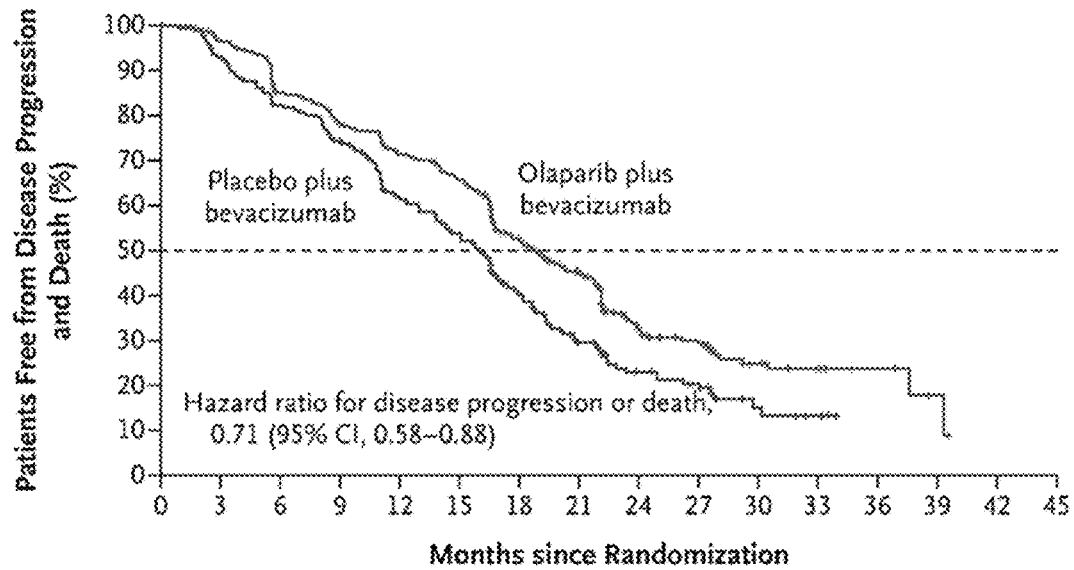
Figure 3C:
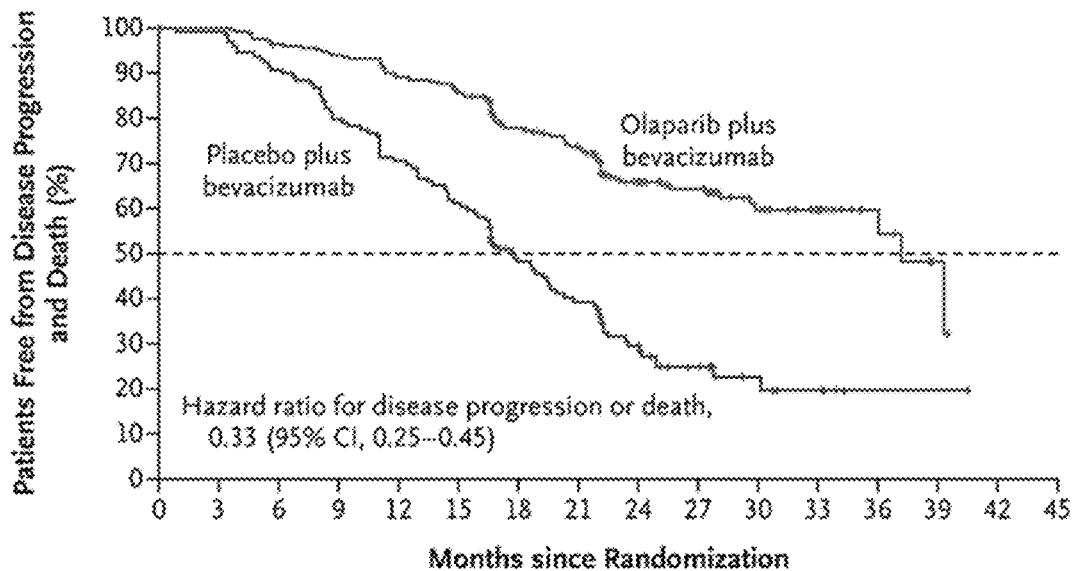
Figure 3D:
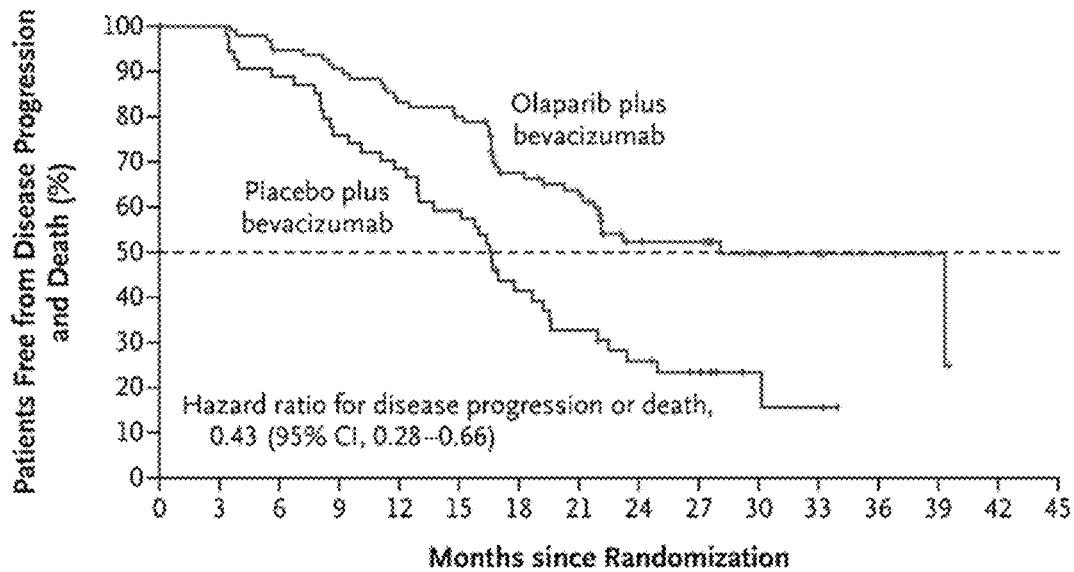

In patients with a tumor BRCA mutation, the median progression-free survival was 37.2 months in the olaparib group and 21.7 months in the placebo group (hazard ratio for disease progression or death, 0.31; 95% CI, 0.20 to 0.47) (FIG. 3A). In patients without a tumor BRCA mutation, the median progression-free survival was 18.9 months in the olaparib group and 16.0 months in the placebo group (hazard ratio for disease progression or death, 0.71; 95% CI, 0.58 to 0.88) (FIG. 3B). In patients with tumors positive for HRD (tumor score of 42 on the myChoice® HRD Plus assay or tumor BRCA mutation), the median progression-free survival was 37.2 months in the olaparib group and 17.7 months in the placebo group (hazard ratio for disease progression or death, 0.33; 95% CI, 0.25 to 0.45) (FIG. 3C). In patients with HRD-positive tumors that did not have BRCA mutations, the median progression-free survival was 28.1 months in the olaparib group and 16.6 months in the placebo group (hazard ratio for disease progression or death, 0.43; 95% CI, 0.28 to 0.66) (FIG. 3D).

In patients with HRD-negative tumors or whose tumor HRD status was unknown (total, 419 patients), the median progression-free survival was 16.9 months in the olaparib group and 16.0 months in the placebo group (hazard ratio for disease progression or death, 0.92; 95% CI, 0.72 to 1.17) (data not shown). In patients with HRD-negative tumors (277 patients), the median progression-free survival was 16.6 months in the olaparib group and 16.2 months in the placebo group (hazard ratio for disease progression or death, 1.00; 95% CI, 0.75 to 1.35) (data not shown).

The median time until the first subsequent treatment for all patients was 24.8 months in the olaparib group and 18.5 months in the placebo group (hazard ratio, 0.59; 95% CI, 0.49 to 0.71). In an interim analysis of second progression-free survival (data maturity, 39%), the Kaplan-Meier estimate of the rate of freedom from second disease progression and death at 18 months was 79% in the olaparib group and 80% in the placebo group (hazard ratio, 0.86; 95% CI, 0.69 to 1.09) (data not shown).

Hypertension

A similar proportion of patients in each treatment arm reported hypertension at baseline (25.1% of patients in the olaparib/bevacizumab arm and 21.6% of patients in the placebo/bevacizumab arm), which could have been a reflection of a prior medical condition and/or caused by bevacizumab during the patient's first line treatment.

Overall, a total of 531 patients (99.3%) in the olaparib/bevacizumab arm and 256 (95.9%) patients in the placebo/bevacizumab arm reported adverse events (AEs) as determined by Common Terminology Criteria for Adverse Events (CTCAE) (version 4.03). In the olaparib/bevacizumab arm, the most common AEs (reported by ≥20% patients) were nausea, fatigue, hypertension, anaemia, lymphopenia, vomiting and arthralgia. In the placebo/bevacizumab arm, the most common AEs (reported by ≥20% patients) were hypertension, fatigue, arthralgia and nausea. All of the events that were reported at a frequency of 0% in the olaparib/bevacizumab arm and at a percentage point greater frequency than the placebo/bevacizumab arm were known adverse drug reactions (ADRs) for olaparib.

Hypertension was reported at a percentage point greater frequency in the placebo/bevacizumab arm than the olaparib/bevacizumab arm. For example as shown in Table 2, hypertension (15.5%) of CTCAE (Common Terminology Criteria for Adverse Events) Grade ≥3 was reported in ≥5% of patients in the olaparib/bevacizumab arm and hypertension (27.3%) of CTCAE Grade ≥3 reported in ≥5% of patients in the placebo/bevacizumab arm.

Common Terminology Criteria for Adverse Events (CTCAE) (version 4.03) defines Grade 1 hypertension as having systolic BP 120-139 mmHg or diastolic BP 80-89 mm Hg; Grade 2 as having systolic BP 140-159 mmHg or diastolic BP 90-99 mm Hg, or recurrent or persistent (≥24 hrs) symptomatic increase by >20 mm Hg (diastolic) or to >140/90 mmHg; Grade 3 as having systolic BP≥160 mmHg or diastolic BP≥100 mmHg; Grade 4 hypertension as having life-threatening consequences, e.g., requiring urgent intervention; and Grade 5 hypertension as death.

TABLE 2

Incidence of hypertension adverse events

| | Number (%) of patients | | | |
|---|---|---|---|---|
| | Overall study duration | | Combination Phase only | |
| | Olaparib/bevacizumab N = 535 | Placebo/bevacizumab N = 267 | Olaparib/bevacizumab N = 534 | Placebo/bevacizumab N = 267 |
| Number of Patients | 308 (57.6) | 136 (50.9) | 267 (50.0) | 116 (43.4) |
| Vascular disorders | 108 (20.2) | 81 (30.3) | 89 (16.7) | 74 (27.7) |
| Hypertension CTCAE Grade 3 or higher | 100 (18.7) | 81 (30.3) | 83 (15.5) | 73 (27.3) |
| Hypertension CTCAE all Grades | 245 (45.8) | 160 (59.9) | | |

In total, 14.9% of patients in the olaparib/bevacizumab arm had a shift from normal to high in systolic blood pressure and 15.5% of patients had a shift from normal to high in diastolic blood pressure. In total, 24.0% of patients in the placebo/bevacizumab arm had a shift from normal to high in systolic blood pressure and 27.0% of patients had a shift from normal to high in diastolic blood pressure. The blood pressure data were in line with the lower incidence of hypertension adverse events reported in the olaparib/bevacizumab arm. Other than the expected increases in systolic and diastolic blood pressure, there were no clinically relevant trends in other vital signs, physical examination observations or electrocardiograms observations in either treatment arm during the study.

An adverse event considered "serious" if, in the view of either the investigator or sponsor, it results in any of the following outcomes: death, a life-threatening adverse event, inpatient hospitalization or prolongation of existing hospitalization, or a persistent or significant incapacity or substantial disruption of the ability to conduct normal life functions. Serious adverse events (SAEs) were reported in 167 patients (31.2%) in the olaparib/bevacizumab arm and 83 patients (31.1%) in the placebo/bevacizumab arm. Most SAEs were reported in less than 1% of patients in each arm. While the hypertension was the most common SAE, its incidence was far lower in the olaparib/bevacizumab arm than in placebo/bevacizumab arm as provided in Table 3.

TABLE 3

Incidence of hypertension serious adverse events

| | Number (%) of patients | | | |
|---|---|---|---|---|
| | Overall study duration | | Combination Phase only | |
| | Olaparib/ bevacizumab N = 535 | Placebo/ bevacizumab N = 267 | Olaparib/ bevacizumab N = 534 | Placebo/ bevacizumab N = 267 |
| Number of Patients | 167 (31.2) | 83 (31.1) | 130 (24.3) | 67 (25.1) |
| Vascular disorders | 56 (10.5) | 35 (13.1) | 45 (8.4) | 32 (12.0) |
| Hypertension | 48 (9.0) | 35 (13.1) | 38 (7.1) | 32 (12.0) |

The benefits of the methods of the disclosure on hypertension are also evident from the use of concomitant medication. The most common concomitant study medications were antibiotics, antihypertensive drugs, and antiemetic agents. As provided in Table 4, the categories of concomitant medications were generally balanced apart from: a lower proportion of patients on the olaparib/bevacizumab received antihypertensive drugs, and a higher proportion of patients on the olaparib/bevacizumab received antiemetic agents or a red blood cell transfusion.

TABLE 4

Allowed concomitant medications during study treatment (FAS)

| | Number (%) of patients | | |
|---|---|---|---|
| | Olaparib/ bevacizumab N = 535 | Placebo/ bevacizumab N = 267 | Total N = 806 |
| Number of patients with any allowed concomitant medication | 433 (80.6) | 193 (71.7) | 626 (77.7) |
| Antibiotic | 244 (45.4) | 116 (43.1) | 360 (44.7) |
| Antihypertensive drug | 142 (26.4) | 110 (40.9) | 252 (31.3) |
| Continuous or intermittent antiemetic agent | 192 (35.8) | 45 (16.7) | 237 (29.4) |
| Anticoagulant | 85 (15.8) | 33 (12.3) | 118 (14.6) |
| Red blood cell transfusion | 100 (18.6) | 4 (1.5) | 104 (12.9) |
| Erythropoietin | 30 (5.6) | 3 (1.1) | 33 (4.1) |
| Granulocyte-colony stimulating factor | 7 (1.3) | 4 (1.5) | 11 (1.4) |
| Platelet transfusion | 5 (0.9) | 1 (0.4) | 6 (0.7) |

Proteinuria

Proteinuria is also a known adverse drug reaction for bevacizumab. As with hypertension, proteinuria was reported at ≥5 a percentage point greater frequency in the placebo/bevacizumab arm than the olaparib/bevacizumab arm.

Common Terminology Criteria for Adverse Events (CTCAE) (version 4.03) defines Grade 1 proteinuria as urine dipstick 1+ or <1.0 grams of protein per 24 hours; Grade 2 as urine dipstick 2+ or 1.0-3.4 grams of protein per 24 hours; Grade 3 as urine dipstick 4+ or ≥3.5 grams of protein per 24 hours.

Adverse drug reactions of proteinuria were observed in a higher percentage of patients in the placebo/bevacizumab arm (41 patients [15.4%]) than in the olaparib/bevacizumab arm (31 patients [5.8%]) as provided in Table 5. While the majority of patients in both treatment arms with negative, trace or 1+ protein (CTCAE Grade 1 proteinuria) by dipstick urinalysis at baseline did not experience an increase in proteinuria beyond 1+ at any individual visit during treatment, a slightly higher proportion of patients on the placebo/bevacizumab arm had an increase in proteinuria to 2+, 3+ or 4+ from baseline when compared with those on olaparib/bevacizumab arm.

TABLE 5

Incidence of proteinuria adverse events

| | Number (%) of patients | | | |
|---|---|---|---|---|
| | Overall study duration | | Combination Phase only | |
| | Olaparib/ bevacizumab N = 535 | Placebo/ bevacizumab N = 267 | Olaparib/ bevacizumab N = 534 | Placebo/ bevacizumab N = 267 |
| Proteinuria CTCAE all Grades | 31 (5.8) | 40 (15.0) | 26 (4.9) | 36 (13.5) |
| Proteinuria CTCAE Grade 3 or higher | 5 (0.9) | 1 (0.4) | | |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method for treating ovarian cancer, fallopian tube cancer, primary peritoneal cancer, breast cancer, and/or pancreatic cancer in a subject, the method comprising:
administering to the subject a therapeutically effective amount of bevacizumab, and
administering to the subject a therapeutically effective amount of 4-[(3-{[4-(cyclopropane-carbonyl)piperazine-1-yl]carbonyl}-4-fluorophenyl)methyl]-2H-phthalazin-1-one (olaparib), or a hydrate, solvate, or prodrug thereof,
wherein the therapeutically effective amount of bevacizumab is in the range of about 10 to 20 mg/kg of body weight every 3 weeks;
wherein the therapeutically effective amount of olaparib is about 300 mg twice daily;
wherein the therapeutically effective amount of olaparib reduces Common Terminology Criteria for Adverse Events (CTCAE) Grade 2, Grade 3, or Grade 4 hypertension in the subject as compared to hypertension in the subject when the subject receives bevacizumab alone; and
wherein the progression free survival is at least about 4 months greater than for subjects receiving bevacizumab alone.

2. The method of claim 1 for treating ovarian cancer or breast cancer.

3. The method of claim 1, wherein the cancer is homologous recombination deficient (HRD) cancer.

4. The method of claim 3, wherein the homologous recombination (HR) gene mutation is selected from BRCA1, BRCA2, ATM, BRIP1, BARD1, CDK12, CHEK1, CHEK2, FANCL, PALB2, PPP2R2A, RAD51B, RAD51C, RAD51D, and RAD54L gene mutation.

5. The method of claim 1, wherein the cancer cells comprise a BRCA1, a BRCA2, and/or an ATM gene mutation.

6. The method of claim 1, wherein the cancer cells comprise a BRCA1 and/or a BRCA2.

7. The method of claim 1, wherein the cancer comprises a tBRCA mutation.

8. The method of claim 1, wherein the cancer is advanced epithelial ovarian cancer.

9. The method of claim 1, wherein the cancer is high-grade endometrioid ovarian cancer.

10. The method of claim 1, wherein the cancer is epithelial ovarian cancer comprising a gBRCA1 or a gBRCA2 mutation.

11. The method of claim 1, wherein the progression free survival is about 4 to 6 months greater.

12. The method of claim 1, wherein the subject previously completed a first line platinum- and/or taxane-based chemotherapy.

13. The method of claim 12, wherein the subject previously received between 6 and 9 cycles of first line platinum- and/or taxane-based chemotherapy.

14. The method of claim 12, wherein the subject received a last cycle of first line platinum- and/or taxane-based chemotherapy between 3 weeks and 9 weeks prior to administering olaparib.

15. The method of claim 12, wherein the subject previously received at least 3 cycles of bevacizumab in combination with the first line platinum- and/or taxane-based chemotherapy.

16. The method of claim 1, wherein the therapeutically effective amount of bevacizumab is about 15 mg/kg of body weight every 3 weeks.

17. The method of claim 1, wherein bevacizumab is administered at no more than 22 cycles in total.

18. The method of claim 1, further comprising identifying the subject having hypertension.

19. The method of claim 18, wherein the hypertension is at least Grade 3 as determined by CTCAE.

20. The method of claim 1, wherein the progression free survival is at least about 12 months greater, when the cancer comprises BRCA gene mutation.

21. The method of claim 1, wherein the progression free survival is at least about 10 months greater when the cancer is homologous recombination deficiency positive (HRD+) cancer.

22. The method of claim 1, wherein the progression free survival is about 15 to 25 months greater when the cancer is HRD+ cancer comprising BRCA gene mutation.

23. The method of claim 1, wherein the therapeutically effective amount of olaparib prevents developing Common Terminology Criteria for Adverse Events (CTCAE) Grade 2, Grade 3, or Grade 4 hypertension.

* * * * *